United States Patent
Thakur et al.

(10) Patent No.: US 11,723,545 B2
(45) Date of Patent: Aug. 15, 2023

(54) AMBULATORY DEHYDRATION MONITORING DURING CANCER THERAPY

(71) Applicant: Boston Scientific Scimed, Inc., Maple Grove, MN (US)

(72) Inventors: Pramodsingh Hirasingh Thakur, Woodbury, MN (US); Jeffrey E. Stahmann, Ramsey, MN (US); Viktoria A. Averina, Shoreview, MN (US); Deepa Mahajan, North Oaks, MN (US); Bruce R. Forsyth, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 241 days.

(21) Appl. No.: 17/115,503

(22) Filed: Dec. 8, 2020

(65) Prior Publication Data
US 2021/0204874 A1    Jul. 8, 2021

Related U.S. Application Data

(60) Provisional application No. 62/956,460, filed on Jan. 2, 2020.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0537* (2013.01); *A61B 5/1116* (2013.01); *A61B 5/1118* (2013.01); *A61B 5/4875* (2013.01); *A61B 5/7282* (2013.01); *A61B 7/00* (2013.01); *A61B 5/024* (2013.01); *A61B 5/0816* (2013.01)

(58) Field of Classification Search
CPC ... A61B 5/0205; A61B 5/0537; A61B 5/1116; A61B 5/1118; A61B 5/4875; A61B 5/7282; A61B 7/00; A61B 5/024; A61B 5/0816; A61B 5/4839; A61B 5/01; A61B 5/087; A61B 7/04; A61B 2562/0204; A61B 2562/0219
See application file for complete search history.

(56) References Cited

U.S. PATENT DOCUMENTS

| | | | |
|---|---|---|---|
| 6,120,442 A | 9/2000 | Hickey | |
| 7,387,610 B2 | 6/2008 | Stahmann et al. | |

(Continued)

OTHER PUBLICATIONS

"U.S. Appl. No. 16/515,740, Notice of Allowance dated Aug. 10, 2022", 9 pgs.

(Continued)

*Primary Examiner* — Catherine M Voorhees
(74) *Attorney, Agent, or Firm* — Schwegman Lundberg & Woessner, P.A.

(57) ABSTRACT

Systems and methods to determine an indication of patient dehydration are disclosed, including receiving first and second physiologic information of a patient, the first physiologic information including heart sound information of the patient and the second physiologic information different than the first physiologic information, and determining the indication of patient dehydration using the received first and second physiologic information.

20 Claims, 5 Drawing Sheets

(51) Int. Cl.
*A61B 5/0537* (2021.01)
*A61B 5/11* (2006.01)
*A61B 7/00* (2006.01)
*A61B 5/08* (2006.01)
*A61B 5/024* (2006.01)

(56) References Cited

U.S. PATENT DOCUMENTS

| | | | |
|---|---|---|---|
| 7,488,290 | B1 | 2/2009 | Stahmann et al. |
| 9,220,444 | B2 | 12/2015 | Russell |
| 10,159,439 | B2 | 12/2018 | Hyde et al. |
| 10,231,667 | B2 | 3/2019 | Mathew et al. |
| 10,368,794 | B2 | 8/2019 | Ionescu et al. |
| 10,405,819 | B2 | 9/2019 | Arima |
| 10,998,101 | B1* | 5/2021 | Tran ............... G16H 20/60 |
| 11,523,743 | B2 | 12/2022 | Thakur et al. |
| 2005/0136125 | A1* | 6/2005 | Roth ............... A01N 1/0226 514/706 |
| 2006/0155204 | A1 | 7/2006 | Wariar et al. |
| 2006/0287604 | A1 | 12/2006 | Hickey |
| 2011/0245711 | A1* | 10/2011 | Katra ............... A61N 1/00 600/547 |
| 2014/0323836 | A1* | 10/2014 | Kusukame ............... A61B 5/68 600/300 |
| 2016/0354032 | A1* | 12/2016 | Wariar ............... A61B 5/4875 |
| 2018/0325431 | A1 | 11/2018 | Guarin et al. |
| 2019/0104989 | A1 | 4/2019 | Breaux et al. |
| 2019/0274655 | A1 | 9/2019 | Thakur et al. |
| 2020/0037887 | A1 | 2/2020 | Thakur et al. |
| 2020/0143917 | A1* | 5/2020 | Sharma ............... G16H 20/60 |

OTHER PUBLICATIONS

"U.S. Appl. No. 16/515,740, Response filed Mar. 10, 2022 to Restriction Requirement dated Jan. 13, 2022", 8 pgs.

"U.S. Appl. No. 16/515,740, Restriction Requirement dated Jan. 13, 2022", 8 pgs.

Burroughs, Robert W., et al., "Significance of Abnormal Phase II Response to Valsalva Maneuver in Cardiac Patients", Circulation. 1956;14:72-76.

Nwazue, Victor C., et al., "Confounders of Vasovagal Syncope: Orthostatic Hypotension", Cardiol Clin. Feb. 2013; 31(1): 89-100. doi:10.1016/j.ccl.2012.09.003.

Singh, Mohita, "Valsalva ratio: Assessment of autonomic modulation in patients of cervical spondylosis", IAIM, 2016; 3(6): 107-112.

U.S. Appl. No. 16/515,740 U.S. Pat. No. 11,523,743, filed Jul. 18, 2019, Ambulatory Monitoring of Physiologic Response to Valsalva Maneuver.

U.S. Appl. No. 18/074,605, filed Dec. 5, 2022, Ambulatory Monitoring of Physiologic Response to Valsalva Maneuver.

* cited by examiner

AMBULATORY DEHYDRATION MONITORING DURING CANCER THERAPY

CLAIM OF PRIORITY

This application claims the benefit of priority under 35 U.S.C. § 119(e) of U.S. Provisional Patent Application Ser. No. 62/956,460, filed on Jan. 2, 2020, which is herein incorporated by reference in its entirety.

TECHNICAL FIELD

This document relates generally to medical devices, and more particularly, but not by way of limitation, to systems and methods for ambulatory dehydration monitoring, such as for patients undergoing cancer therapy.

BACKGROUND

Cancer is a major worldwide public health concern and the second leading cause of death in the United States. 1.7 million new cancer cases and over 600,000 cancer deaths are projected to occur in 2018. With early detection and improved therapy, cancer survivorship reached 14.5 million patients in 2014, and is projected to exceed 19 million by 2024.

Side effects of chemotherapy treatments vary from patient-to-patient, depending on the type of medication and length of treatment. For example, anthracyclines, cyclophosphamide, and trastuzumab may impact cardiac function (e.g., contractility). Other medications, such as imatinib, impact cardiac decompensation by altered preload (e.g., fluid retention). Bevacizumab may impact cardiac decompensation by altered afterload (e.g., hypertension). Ifosfamide may impact heart rate and arrhythmias. 5-cisplatin and 5-fluorouracil may impact cerebrovascular disease (e.g., ischemia risk), etc.

Cardiotoxicity is the occurrence of heart electrophysiology dysfunction or muscle damage resulting in a weak and inefficient cardiac supply, and is often a result of cancer treatment, affecting between 5% and 65% of cancer treatment patients. Cardiotoxicity is currently monitored by point-of-care diagnostics, and largely after cancer treatment.

Chemotherapy is a type of widely used cancer therapy known for its efficacy as well as side effects. Cardiovascular dysfunctions are among the significant side effects of chemotherapy drugs. For example, anthracyclines are a class of chemotherapy agents (e.g., doxorubicin, daunorubicin, idarubicin, and epirubicin) commonly applied to treat various types of cancers while being particularly known for cardiotoxicity. Measurable cardiac dysfunctions have been reported in many cancer patients receiving anthracycline-based chemotherapies. Cardiac damage due to the cardiotoxicity is believed to create an underlying substrate for later progression of left ventricular dysfunction (e.g., measured by low ejection fraction) and heart failure. Mortality during and after chemotherapies can be significantly increased by cardiovascular diseases including congestive heart failure.

Ambulatory medical devices (AMDs), including implantable, subcutaneous, wearable, external, or one or more other medical devices, etc., have been used to monitor, detect, or treat various conditions, including heart failure (HF), atrial fibrillation (AF), etc. AMDs may include sensors to sense physiological signals from a patient. Frequent patient monitoring and early detection of worsening patient condition, including worsening heart failure (WHF) or AF, may help improve patient outcome. Identification of patients or groups of patients at an elevated risk of future adverse events may help provide timely patient treatment or prevent or reduce patient hospitalization. Identifying and safely managing patient risk of worsening condition may avoid unnecessary medical interventions or hospitalizations and reduce healthcare costs.

AMDs can be configured to receive physiologic information, including cardiac electrical information, associated with various implantable or external locations of a patient. For example, certain AMDs are configured to receive cardiac electrical information from implantable electrodes located within or on the heart, including coupled to a lead and located in one or more chambers of the heart or within the vasculature of the heart near one or more chambers. Certain AMDs include one or more atrial leads, or receive information from one or more atrial leads, configured to be located in a right atrium of a patient. Other AMDs do not include an atrial lead or electrode in the right atrium. Detection of atrial events, such as atrial depolarizations, can be challenging without information from an atrial lead or an electrode in the right atrium.

SUMMARY

Systems and methods to determine an indication of patient dehydration, such as using one or more ambulatory medical devices (AMDs), are disclosed, including receiving physiologic information of a patient, including first physiologic information, such as heart sound information of the patient, and second physiologic information different than the first physiologic information. The indication of patient dehydration (e.g., increased patient dehydration) can be determined using the received first and second physiologic information. In certain examples, the first and second physiologic information can include qualified or unqualified physiologic information.

An example (e.g., "Example 1") of subject matter (e.g., a system) for determining patient dehydration during cancer therapy may comprise a signal receiver circuit configured to receive first and second physiologic information of a patient, the first physiologic information comprising heart sound information of the patient, and the second physiologic information different than the first physiologic information; and an assessment circuit configured to determine an indication of patient dehydration (e.g., increased patient dehydration) using the received first and second physiologic information.

In Example 2, the subject matter of Example 1 may optionally be configured such that the assessment circuit is configured to determine the indication of patient hydration using the first physiologic information in response to the second physiologic information meeting a predetermined criterion.

In Example 3, the subject matter of any one or more of Examples 1-2 may optionally be configured such that the heart sound information of the patient comprises third heart sound (S3) information of the patient, the second physiologic information comprises impedance information of the patient, and the assessment circuit is configured to determine the indication of patient hydration using the impedance information when a change in S3 information is below a threshold.

In Example 4, the subject matter of any one or more of Examples 1-3 may optionally be configured such that the heart sound information of the patient comprises second heart sound (S2) information of the patient, the second physiologic information comprises at least one of posture or activity information of the patient, the assessment circuit is configured to determine the indication of patient hydration using the S2 information of the patient when the posture information indicates a change in patient posture or when the activity information indicates that patient activity is below a threshold.

In Example 5, the subject matter of any one or more of Examples 1-3 may optionally be configured such that the heart sound information comprises second heart sound (S2) information of the patient, and the second physiologic information comprises at least one of heart rate information of the patient, respiration information of the patient, impedance information of the patient, or chemical information of the patient.

In Example 6, the subject matter of any one or more of Examples 1-3 may optionally be configured such that the signal receiver circuit is configured to receive at least one of respiration information of the patient or impedance information of the patient, and, to determine the patient dehydration, the assessment circuit is configured to determine an indication of patient vomiting using the first physiologic information and the respiration information of the patient or the impedance information of the patient.

In Example 7, the subject matter of any one or more of Examples 1-3 may optionally be configured such that the assessment circuit is configured to trigger patient confirmation of a candidate patient vomiting event using the determined indication of patient vomiting.

In Example 8, the subject matter of any one or more of Examples 1-3 may optionally be configured such that the assessment circuit is configured to count candidate patient vomiting events using determined indications of patient vomiting, and to adjust the determined indication of patient hydration using the count of candidate patient vomiting events.

In Example 9, the subject matter of any one or more of Examples 1-3 may optionally be configured such that the signal receiver circuit is configured to receive heart rate (HR) information of the patient, and, to determine the patient dehydration, the assessment circuit is configured to determine an indication of patient diarrhea using the first physiologic information and the heart rate (HR) information of the patient.

In Example 10, the subject matter of any one or more of Examples 1-3 may optionally be configured such that the assessment circuit is configured to trigger patient confirmation of a candidate diarrhea events using the determined indication of patient diarrhea.

In Example 11, the subject matter of any one or more of Examples 1-3 may optionally be configured such that the assessment circuit is configured to count candidate patient diarrhea events using determined indications of patient diarrhea, and to adjust the determined indication of patient hydration using the count of candidate patient diarrhea events.

In Example 12, the subject matter of any one or more of Examples 1-3 may optionally be configured to comprise an implantable medical device comprising a heart sound sensor, wherein, to determine the patient dehydration, the assessment circuit is configured to determine an indication of patient vomiting and an indication of patient diarrhea using the first physiologic information.

An example (e.g., "Example 13") of subject matter (e.g., a method) for determining patient dehydration during cancer therapy comprises receiving, using a signal receiver circuit, first and second physiologic information of a patient, the first physiologic information comprising heart sound information of the patient, and the second physiologic information different than the first physiologic information; and determining, using an assessment circuit, an indication of patient dehydration using the received first and second physiologic information.

In Example 14, the subject matter of Example 13 may optionally be configured such that the assessment circuit is configured to determine the indication of patient hydration using the first physiologic information in response to the second physiologic information meeting a predetermined criterion, the heart sound information of the patient comprises third heart sound (S3) information of the patient, the second physiologic information comprises impedance information of the patient, the predetermined criterion comprises when a change in the S3 information is below a threshold, and the assessment circuit is configured to determine the indication of patient hydration using the impedance information when the change in S3 information is below the threshold.

In Example 15, the subject matter of any one or more of Examples 13-14 may optionally be configured such that the assessment circuit is configured to determine the indication of patient hydration using the first physiologic information in response to the second physiologic information meeting a predetermined criterion, the heart sound information of the patient comprises second heart sound (S2) information of the patient, the second physiologic information comprises at least one of posture or activity information of the patient, the predetermined criterion comprises when the posture information indicates a change in patient posture or when the activity information indicates that patient activity is below a threshold, and the assessment circuit is configured to determine the indication of patient hydration using the S2 information of the patient when the posture information indicates the change in patient posture or the activity information indicates that patient activity is below the threshold.

In Example 16, the subject matter of any one or more of Examples 13-15 may optionally be configured to comprise receiving, using the signal receiver circuit, at least one of respiration information of the patient or impedance information of the patient, wherein determining the indication of patient dehydration comprises determining an indication of patient vomiting using the first physiologic information and the respiration information of the patient or the impedance information of the patient.

In Example 17, the subject matter of any one or more of Examples 13-16 may optionally be configured to comprise triggering, using the assessment circuit, patient confirmation of a candidate patient vomiting event using the determined indication of patient vomiting.

In Example 18, the subject matter of any one or more of Examples 13-17 may optionally be configured to comprise counting, using the assessment circuit, candidate patient vomiting events using determined indications of patient vomiting; and adjusting, using the assessment circuit, the determined indication of patient hydration using the count of candidate patient vomiting events.

In Example 19, the subject matter of any one or more of Examples 13-18 may optionally be configured to comprise receiving, using the signal receiver circuit, heart rate (HR) information of the patient, wherein determining the patient dehydration comprises determining an indication of patient diarrhea using the first physiologic information and the heart rate (HR) information of the patient.

In Example 20, the subject matter of any one or more of Examples 13-19 may optionally be configured to comprise counting, using the assessment circuit, candidate patient diarrhea events using determined indications of patient diarrhea; and adjusting, using the assessment circuit, the determined indication of patient hydration using the count of candidate patient diarrhea events.

In an example, determining the indication of patient dehydration can include determining one or more of an indication of patient vomiting or patient diarrhea, such as using the first physiologic information in combination with the second or other received physiologic information.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
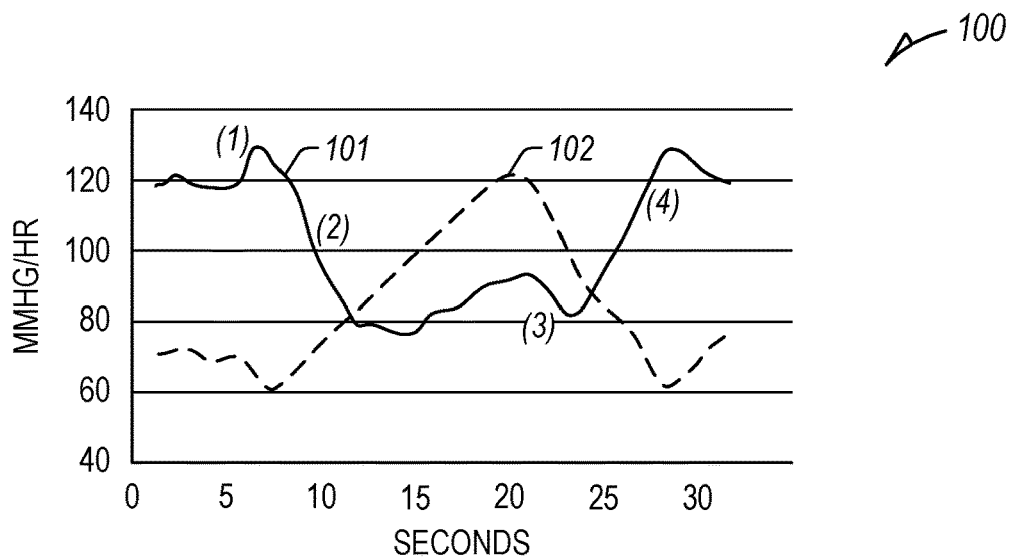
FIG. 1 illustrates an example relationship between systolic blood pressure and heart rate during a Valsalva maneuver.

Dehydration is a common side-effect of chemotherapy. Chemotherapy-induced nausea and vomiting (CINV) and chemotherapy-induced diarrhea (CID) are two of the most common risk factors for developing dehydration during cancer therapy. Reported incidence of CINV is 20-30% in chemotherapy patients, even despite prophylaxis. Reported incidence of CID in chemotherapy patients is higher, as high as 82%, with up to 33% of chemotherapy patients experiencing severe (grade 3 or 4) diarrhea.

Dehydration, especially that resulting from CID, severely interferes with cancer therapy, resulting in treatment alterations in approximately 60% of patients, a reduction in treatment dosage in 22% of patients, a delay in dosage in 28% of patients, and complete termination of treatment in 15% of patients. Moreover, dehydration can last as long as 10 years post-treatment, and can be especially aggravating to cancer patients, as in many instances, dehydration can result in a lack of appetite and thirst, further weakening an already-vulnerable population.

The present inventors have recognized, among other things, systems and methods, including specific combinations of ambulator sensors and monitoring, to detect and provide early indications of dehydration, such that the negative effects of dehydration can be reduced or more quickly or accurately counteracted, such that interference with cancer therapy can be reduced, improving patient outcomes and increasing medical system and medical device efficiency. Such ambulatory sensors are often employed in existing medical device systems, such that the systems and methods disclosed herein provide additional capabilities to such existing medical device systems, ambulatory sensors, or methods employed, in certain examples, for different therapies, such as cardiac rhythm therapies, heart failure management, etc.

Vomiting is experienced as a finale of a series of three events: nausea; retching; and emisis or vomition. Nausea typically involves an unpleasant and difficult to describe physiologic experience, often including decreased gastric motility, increased tone in the small intestine, or often reverse peristalsis in the proximal small intestine. Retching, or dry heaves, are spasmodic respiratory movements conducted with a closed glottis, where the antrum of the stomach contracts while fundus and cardia relax, and herniation of the abdominal esophagus and cardia into the thoracic cavity occurs due to negative pressure, or inspiratory efforts with a closed glottis. In contrast, emisis or vomition are a highly coordinated series of events.

In emisis or vomition, a deep breath is taken, the glottis is closed, the larynx is raised to open the upper esophageal sphincter, and the soft palate is elevated to close off the posterior nares. The diaphragm is contracted sharply downward to create negative thoracic pressure in the thorax, facilitating opening of the esophagus and distal esophageal sphincter. Simultaneously with downward movement of the diaphragm, the muscles of the abdominal walls are vigorously contracted, squeezing the stomach and elevating intragastric pressure. With the pylorus closed and the esophagus relatively open, the route of exit is clear.

In certain examples, direct measurement of thoracic or abdominal pressure (including intrathoracic or intraabdominal pressure) may not be available. The present inventors have recognized that, in certain examples, other physiologic information can be used to determine an indication of thoracic or abdominal pressure, such as heart sounds.

Heart sounds are recurring mechanical signals associated with cardiac vibrations from blood flow through the heart with each cardiac cycle, and can be separated and classified according to activity associated with the vibrations and blood flow. Heart sounds include four major sounds: the first through the fourth heart sounds. The first heart sound (S1) is the vibrational sound made by the heart during closure of the atrioventricular (AV) valves, the mitral valve and the tricuspid valve, at the beginning of systole. The second heart sound (S2) is the vibrational sound made by the heart during closure of the aortic and pulmonary valves at the beginning of diastole. The third and fourth heart sounds (S3, S4) are related to filling pressures of the left ventricle during diastole.

Specifically, with respect to intrathoracic pressure, a decreased intrathoracic pressure during inspiration decreases S and increases S2. Thus, S1 and S2 changes can be used to determine indications of intrathoracic pressure changes. Accordingly, the present inventors have recognized that changes in S1 and S2 can be used to detect candidate vomiting events. In an example, respiration phase can be detected using a respiration sensor (e.g., an impedance sensor, an air flow sensor, an accelerometer, etc.). An aggregate (e.g., combined) increase in S2 and decrease in S1 during inspiration (e.g., one inspiration phase, successive inspiration phases, or first number of successive or proximate inspiration phases, etc.) above a baseline (e.g., a short-term average longer than the first number of inspiration phases, a long-term average, or one or more other baselines, etc.) can be used to detect candidate vomiting events.

In certain examples, other information can be used to supplement detection of or confirm candidate vomiting events. For example, patients commonly lean forward while vomiting. A posture sensor can be used to supplement or confirm candidate vomiting events, such as by detecting a forward lean or change in posture during a detected decrease in intrathoracic pressure during inspiration. Further, after or proximate to the candidate vomiting episode, an increase in heart rate (HR) and respiration rate can be used to supplement or confirm candidate vomiting events. In other examples, candidate vomiting events can be detected using one or more sensors (e.g., pressure sensors, accelerometers, acoustic sensors, heart sound sensors, respiration sensors, heart rate sensors, etc.) and confirmed using patient feedback (e.g., confirmation by the patient, such as using input to a mobile device, verbal feedback, or by one or more other caregivers, clinicians, etc.).

Detection or confirmation of candidate vomiting events can be used to track or count the number of vomiting events, such as to establish a severity scale of vomiting, such as to monitor dehydration, etc. A length of respiratory pause coincident with a candidate vomiting event can be used to determine an indication of volume of fluid ejected. The determined indication of volume of fluid ejected can be used to determine the severity scale of vomiting. Changes in physiological information can be tracked, within a day (e.g., disturbance in circadian pattern), day-to-day (e.g., upward trends), or both, to detect early indications of dehydration. Further, sensor response to changes in posture can be used to detect early indications of dehydration.

Clinical management of diarrhea is based on severity grades ranging from Grade 1, a mild increase in stools per day (e.g., <4 over baseline), to Grade 5, which is death. Grades 1 and 2 (without additional symptoms) are generally classified as uncomplicated CID managed by modification of diet and administration of anti-diarrheal medication. Grades 3 and 4 are generally classified as complicated CID requiring aggressive high-dose anti-diarrheal medication often hospitalization. Grade 1 or 2 diarrhea with additional symptoms, such as cramping, nausea/vomiting, fever, sepsis, neutropenia, frank bleeding, or dehydration, are often re-classified and treated as complicated CID.

TABLE 1

Diarrhea Grades

| | Grade | | | | |
|---|---|---|---|---|---|
| | 1 | 2 | 3 | 4 | 5 |
| | Increase of <4 stools per day over baseline; mild | Increase of 4-6 stools per day over baseline; moderate | Increase of ≥7 stools per day over baseline; incontinence; hospitalization indicated; severe | Live-threatening conse-quences; urgent intervention | Death |
| | increase in ostomy output over baseline | increase in ostomy output over baseline | increase in ostomy output over baseline; limiting self care activities of daily living (ADL) | indicated | |
| Type | Uncomplicated (without additional symptoms) | | Complicated (or Grades 1 or 2 with additional symptoms, such as cramping, nausea/vomiting, fever, sepsis, neutropenia, frank bleeding, or dehydration) | | |

Diarrhea, as a medical symptom, and especially outside of the context of an existing hospitalization, is often self-reported. Unless occurrence is severe, patients often choose not to report, or under-report, in certain instances due to the sensitive nature of the condition, but often due to a lack of perceived immediacy or importance to the patient's overall medical condition. Without being specifically asked by a clinician or caregiver, such conditions are often not reported or recorded, and very seldomly reported in real-time, and thus are not accounted for in determining ambulatory patient status. The systems and methods disclosed herein can provide ambulatory and automated detection and monitoring of patient diarrhea, improving detection of patient dehydration risk, often before such conditions become complicated.

A Valsalva maneuver is a moderately forceful attempted exhalation against a closed airway, such as the act of blowing up a balloon. Patients typically invoke a Valsalva maneuver during defecation (the feeling/act of pushing within the abdomen). Detection of a Valsalva maneuver can be used to chronically monitor defecation in patients.

FIG. 1 illustrates an example relationship 100 between systolic blood pressure 101 in millimeters of Mercury (mmHg) and heart rate 102 in beats per minute (BPM) during a Valsalva maneuver. Blood pressure is the pressure of circulating blood on the walls of blood vessels, and typically refers to the pressure in large arteries of the systemic system. When further specified, such as left ventricular (LV) pressure, etc., such pressure refers to the pressure in that physiologic component. Blood pressure is commonly expressed in terms of systolic and diastolic pressure. Systolic pressure refers to the maximum pressure during a heart contraction, and diastolic pressure refers to the minimum pressure between to heart contractions.

There are four phases of a typical response to a Valsalva maneuver: first (1), application of expiratory force causes a pressure rise inside the chest, forcing blood out of the pulmonary circulation into the left atrium, causing a mild rise in stroke volume (heart output) and systolic blood pressure during the first few seconds of the maneuver; second (2), pressure inside the chest reduces venous return, reducing stroke volume and systolic blood pressure, and increasing heart rate (compensatory tachycardia); third (3), the pressure on the chest is released, causing an initial, further decrease in stroke volume, but a subsequent rise in cardiac output; and fourth (4), increased blood return to the heart and a rapid increase in cardiac output, resulting in a temporary increase in stroke volume above a normal level and decrease in heart rate below a normal level before each returning to baseline. Deviation from this typical response can be indicative of abnormal heart function or autonomic control of the heart. Moreover, detection and monitoring of events indicating such response, the indicated systolic blood pressure and heart rate response that coincide with a respiratory pause (a cessation of breathing) can be used to determine a number of stools per day without relying on patient reporting or clinician inquiry.

In an example, occurrences of detected Valsalva maneuvers can be counted (e.g., per day, etc.) and recorded. Information from one or more other sensors can be recorded during such detected occurrences. In certain examples, detections can trigger or prompt separate patient feedback, such as to confirm detected occurrences as stool events. The systems and methods disclosed herein can use such patient feedback to improve ambulatory detection and counting.

In certain examples, direct measurement of systolic blood pressure may not be available. The present inventors have recognized that, in certain examples, other physiologic information can be used to determine an indication of systolic blood pressure, such as heart sounds.

Heart sounds are generally related to blood pressure, such as illustrated in the commonly-assigned Thakur et al. U.S. Patent Application No. 2019/0274655, titled "Chronic Monitoring of Blood Pressure using Heart Sounds", herein incorporated by reference in its entirety including its disclosure of using one or more ambulatory sensors to determine an indication of blood pressure using heart sounds, including, for example, the first heart sounds (S1), the second heart sound (S2), etc. S1 can be indicative of contractility, and S2 can be indicative of blood pressure during periods of median contractility (e.g., S1 within a baseline, such as less than 25% above a patient baseline or long-term average value, etc.), such that an increase in S2 above a patient baseline or long-term average value can be indicative of an increase in blood pressure.

In an example, a detected increase in an indication of abdominal pressure (e.g., using an intraabdominal pressure sensor, etc.) can be used to trigger monitoring of heart sounds, heart rate, etc., such as to confirm a detected candidate Valsalva maneuver. In certain examples, indications of abdominal pressure can be detected using one or more sensors (e.g., a pressure sensor or transducer in the abdomen, such as in the abdomen, bladder, vagina, etc.) as candidate events (e.g., candidate Valsalva maneuver or diarrhea events) and confirmed using additional sensors or other indications of blood pressure, heart rate, etc. In other examples, candidate events can be detected using one or more sensors (e.g., pressure sensors, accelerometers, acoustic sensors, heart sound sensors, heart rate sensors, etc.) and confirmed using patient feedback (e.g., confirmation by the patient, such as using input to a mobile device, verbal feedback, or by one or more other caregivers, clinicians, etc.). In an example, the one or more sensors, such as acoustic sensors, accelerometers, etc., can be used to detect gastrointestinal (GI) mobility, or flow associated with diarrhea. In certain examples, candidate events can be detected using detected GI mobility or flow associated with diarrhea.

Detection or confirmation of candidate events can be used to track the number of stools (stool counts) per day to establish a diarrhea grade. Strength of sensor changes (e.g., S1 drop, heart rate increase) can be used to determine softness, hardness, or water content of each stool. Duration of sensor changes can be used to determine the amount (e.g. volume, weight) of each bowel movement. Impedance changes can be tracked, within a day (e.g., disturbance in circadian pattern), day-to-day (upward trends), or both, to detect early indications of dehydration. Further, impedance sensor response to changes in posture can be used to detect early indications of dehydration.

Detection of indications of increased patient dehydration take place over long periods of time (e.g., months). Accordingly, with respect to patient dehydration, increases and trends can take place over long periods of time, in certain examples, 30 days or greater. Sudden changes with respect to chronic dehydration are still measured as daily values, or short-term averages taken over several days. In contrast, candidate Valsalva or vomiting events take place over seconds or minutes, though often with respect to a longer baseline, including long-term (e.g., 30 days or longer), short-term (e.g., several days, such as 3 days, 7 days, etc., shorter than a long-term period), or daily averages. Accordingly, increases with respect to such candidate Valsalva or vomiting events take place over time periods within that same scale, seconds or minutes, and can be indicative of heightened risk of patient dehydration.

In addition to detected indications of vomiting and diarrhea, other physiological information can be used to detect dehydration in a patient. In an example, detected indications of vomiting and diarrhea can be used to supplement or adjust detected indication of patient dehydration. Alerts can be provided in response to such detections, such as to a physician or caregiver. In other examples, dehydration detection can be changed in response to detected indications of vomiting or diarrhea. For example, in response to detected indications of vomiting or diarrhea, additional sensors or detections (e.g., as described herein, illustrated in FIGS. 2-8, etc.) can be implemented to monitor patient hydration or to determine indications of increased patient dehydration, devoting more system resources to detecting indications of patient dehydration. In one example, a first, chronic, low-power dehydration monitoring mode can be implemented, including monitoring indications of candidate vomiting and diarrhea events. Upon detection of a specified number (e.g., one or more) or type (e.g., candidate, confirmed, unconfirmed, etc.) of candidate vomiting or diarrhea events, a second, high-power dehydration monitoring mode can be implemented, requiring more resources, additional or more expensive (e.g., power or processing) sensors, a higher sampling rate (e.g., transitioning from day-to-day impedance or heart sound dehydration monitoring to within-day impedance or heart sound dehydration monitoring), additional data processing, or higher power than the first low-power dehydration monitoring mode.

In certain examples, multiple indications of physiologic information can be combined to improve detection of dehydration in a patient. The physiologic information can include one or more (or two or more) of daily values, measurements, or trends of impedance (Z) (e.g., intrathoracic impedance), time active (e.g., time active above a threshold, such as detected using an accelerometer and a timer, etc.), rapid shallow breathing index (RSBI), nighttime HR (nHR), heart sounds (e.g., S1, S2, S3, etc.). In other examples, the physiologic information can further include detection of electrolyte disturbances, metabolic acidosis or acidemia (e.g., low plasma bicarbonate ($HCO_3$), increased anion gap, etc.), or extracellular osmotic pressure disturbances.

Implantable or external sensors can enable dehydration detection, such as one or more implantable or external chemical sensors, including an electrolyte sensor (e.g., potassium, sodium, or one or more other electrolyte or chemical sensors), a pH sensor, or an anion gap sensor to sense metabolic acidosis/acidemia. In other examples, one or more implantable or external pressure sensors (e.g., an implantable accelerometer or pressure sensor, an external cuff or photoplethysmogram (PPG) sensor, etc.) can enable dehydration detection, such as an osmotic pressure sensor to sense osmotic pressure disturbances, etc. Other implantable or external sensors are disclosed herein.

Physiologic information used to detect an increase in dehydration can be qualified or unqualified. Qualified physiologic information includes physiologic information considered in response to one or more other qualifying measurements or conditions (e.g., predetermined criterion, etc.), such as a change (or lack of change) in patient condition, status (e.g., activity, posture, sleep state, etc.), or physiologic information. Unqualified physiologic information includes physiologic information itself, not in response to another measurement or condition. Combinations of physiologic information can include combinations of two or more types of unqualified physiologic information, two or more types of qualified physiologic information, or combinations of two or more types of qualified or unqualified physiologic information.

Unqualified physiologic information can include two or more of the following (or one or more of the following in combination with one or more other indication of physiologic information disclosed herein): an increase in tissue impedance (e.g., solid tissue impedance), an increase in blood impedance, an increase in HR, an increase in respiration rate, a decrease in tidal volume (TV), a decrease in activity, an increase in hematocrit, an increase in skin temperature, a decrease in skin elasticity, a decrease in sweat rate, an increase in blood osmolity, an increase in urine osmolity, a change in electrolyte(s), a decrease in blood pressure, a decrease in S2, or a change in pH. Parameters can be selected from different physiological targets (e.g., hemodynamic, electrophysiologic, chemical, respiratory, fluid volume, etc.) and combined to determine one or more composite measurements, taking advantage of efficiency (power efficiency, re-use of existing or otherwise employed sensors, etc.) and diagnostic value considerations.

A reduction in patient fluid associated with dehydration can reduce patient sweat rate, increasing one or more of skin temperature or skin impedance. The patient sweat rate can be detected using a sweat sensor (e.g., a cutaneous sensor measuring temperature or impedance). Information from the sweat sensor can be used to capture electrolyte changes or imbalances in patient sweat.

In other examples, frequency domain analysis of impedance measurements can be analyzed to separate vascular (e.g., hematocrit) fluid status and interstitial fluid status, or one or more other specific impedance measurements. For example, the commonly assigned Stahmann et al. U.S. Pat. No. 7,387,610, titled "Thoracic Impedance Detection with Blood Resistivity Compensation", herein incorporated by reference in its entirety, discloses separate detection of extravascular and intravascular impedance using different frequency components of impedance measurement. Adjusting or removing frequency components of impedance measurements above about 0.05 Hz, etc., such as to isolate DC or near-DC impedance measurements, can separate solid tissue impedance (e.g., extravascular impedance) from blood impedance (e.g., intravascular impedance). Solid tissue impedance can be used to indicate fluid volume.

In contrast, qualified physiologic information can include different series or combinations (e.g., commensurate or overlapping) of detected physiologic information. For example, a combination of physiologic information used to detect dehydration can include an increase in impedance with no change in the third heart sound (S3). S3 and filling pressure are generally a rectified response to fluid. With fluid overload, S3 and filling pressures generally increase. However, with dehydration, the body will compensate and maintain filling pressures even in light of reduced fluid levels, such as by vasoconstriction, etc. Accordingly, an increase in impedance measurements (e.g., tissue impedance), indicating a reduction in body fluid, with maintained S3 (an indication of compensation to maintain filling pressures) can be indicative of an increase in dehydration.

In other examples, a decrease in the second heart sound (S2) with an increase in HR (e.g., nHR) can be indicative of dehydration. A combination of blood pressure, S2 amplitude, and HR response to posture changes can be indicative of dehydration, as posture changes can accentuate sensor changes. A reduction in impedance response to posture changes can be indicative of dehydration, as dehydration reduces blood flow to the periphery, and accordingly, reduces gravity driven movement of fluid with posture changes.

In an example, qualified physiologic information can include physiologic information considered or measured in response to a rapid transient condition (e.g. a change in posture) to assess a physiologic response. Such measurements can be made within the physiological transient response time of such conditions (e.g., during or immediately following (seconds) said posture change, etc.). In other examples, qualified physiologic information can include physiologic information considered or measured in response to a detected steady-state condition, such as during a detected period when activity is below a threshold, when the patient is at rest, etc.

TABLE 2

Dehydration Detection using Qualified Parameters

| Dehydration Indicating Parameter | Qualifying Parameter | Qualifying Condition |
|---|---|---|
| Tissue Impedance | Third Heart Sound (S3) | Use tissue impedance when ΔS3 is less than a threshold (e.g., little to no change in S3) |
| Blood Pressure, Tissue Impedance, Second Heart Sound (S2), Respiration Rate, Heart Rate | Posture | Measure parameter during and/or within physiologic time constant of posture change |
| Blood Pressure, Respiration Rate, Heart Rate, Tidal Volume, Heart Sounds | Activity | Measure parameter when activity level is below a threshold (e.g., during periods of inactivity) |

Figure 2:
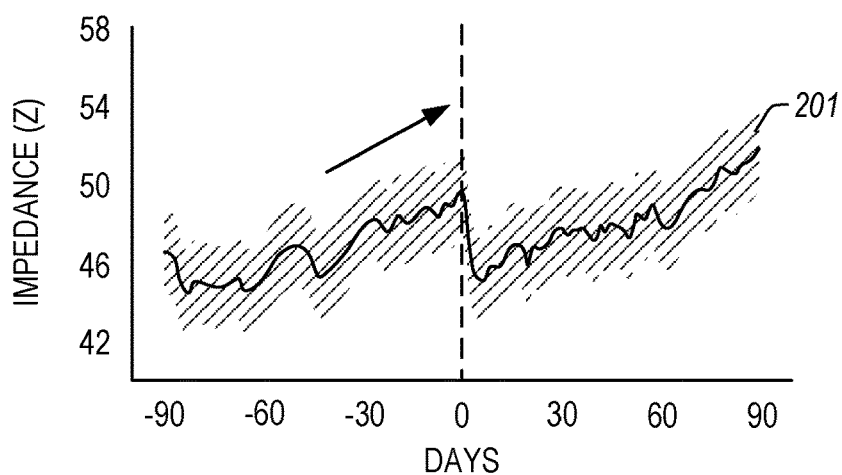
FIGS. 2-8 illustrate example relationships between physiologic information and time (in days) prior to and after a dehydration event (e.g., an adverse event with reported dehydration).

FIGS. 2-8 illustrate example relationships between physiologic information and time (in days) prior to and after a dehydration event (e.g., an adverse event with reported dehydration). FIG. 2 illustrates an example relationship 200 between impedance (Z) (e.g., intrathoracic impedance) 201, including a trend line and variance, over 180 days centered around a dehydration event (day 0). The arrow in FIG. 2 indicates a general upward trend in impedance measurements in the 30 days prior to the dehydration event, which is followed by a sharp decline post-treatment (e.g., days 0-5).

Figure 3:
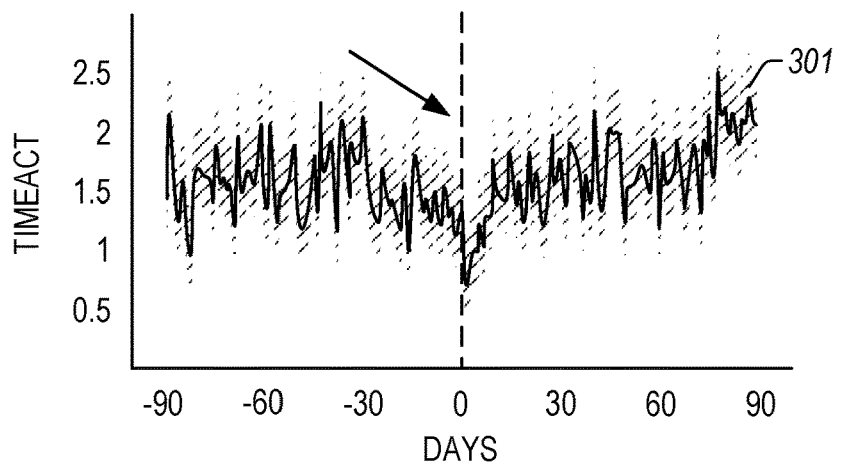

FIG. 3 illustrates an example relationship 300 between time active (TIMEACT) 301, including a trend line and variance, over 180 days centered around a dehydration event (day 0). The arrow in FIG. 3 indicates a general downward trend in time active measurements in the 30 days prior to the dehydration event, which is followed by an initial sharp increase post-treatment (e.g., days 0-3) and ensuing gradual increase (days 3-75).

Figure 4:
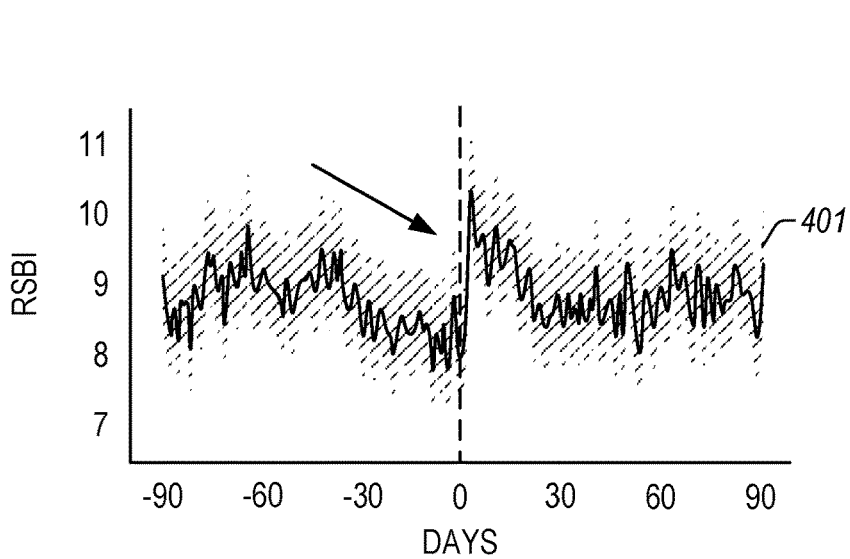

FIG. 4 illustrates an example relationship 400 between rapid shallow breathing index (RSBI) 401, including a trend line and variance, over 180 days centered around a dehydration event (day 0). RSBI is a ratio of respiratory frequency to tidal volume (TV). TV can be measured as an aggregate of respiration changes, such as detected using measured changes in transthoracic impedance. The arrow in FIG. 4 indicates a general downward trend in RSBI measurements in the 30 days prior to the dehydration event, which is followed by an initial sharp increase post-treatment (e.g., days 0-3) and ensuing return to baseline (days 3-25).

Figure 5:
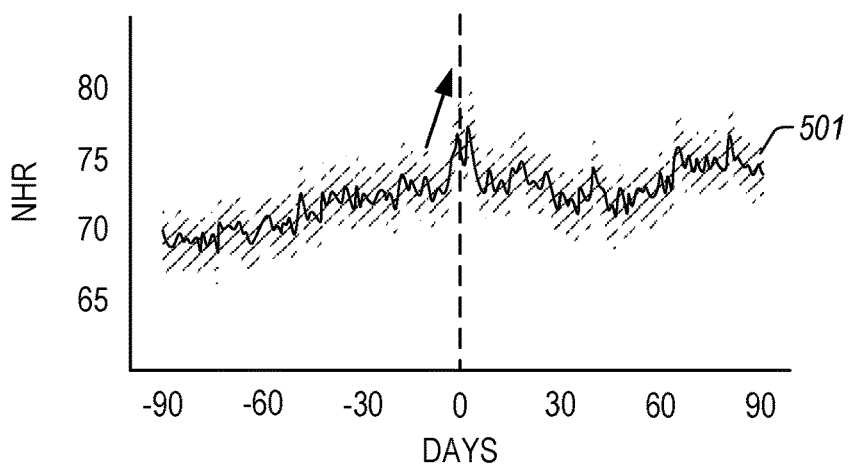

FIG. 5 illustrates an example relationship 500 between nighttime heart rate (nHR) 501, including a trend line and variance, over 180 days centered around a dehydration event (day 0). The arrow in FIG. 5 indicates a sharp upward trend in nighttime heart rate (nHR) measurements in the days (e.g., days −3-0) prior to the dehydration event, which is followed by an initial sharp decrease post-treatment (e.g., days 0-3). In other examples, other HR information, such as an average daily HR, daytime HR, or heart rate associated with one or more other parameters (e.g., posture, activity, etc.) can be indicative of electrophysiologic information and used to detect dehydration. In an example, HR information can be detected using one or more implantable or external electrodes, external PPG sensors, etc.

Figure 6:
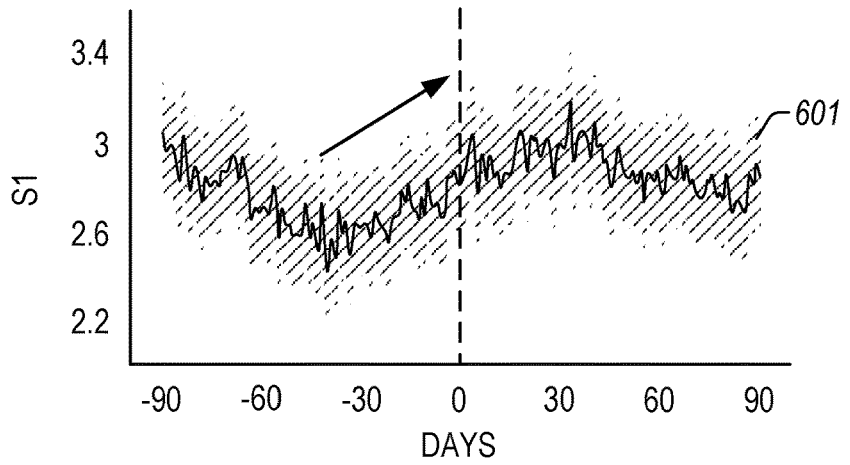

FIG. 6 illustrates an example relationship 600 between the first heart sound (S1) 601, including a trend line and variance, over 180 days centered around a dehydration event (day 0). The arrow in FIG. 6 indicates an upward trend in S measurements in the 30 days prior to the dehydration event.

Figure 7:
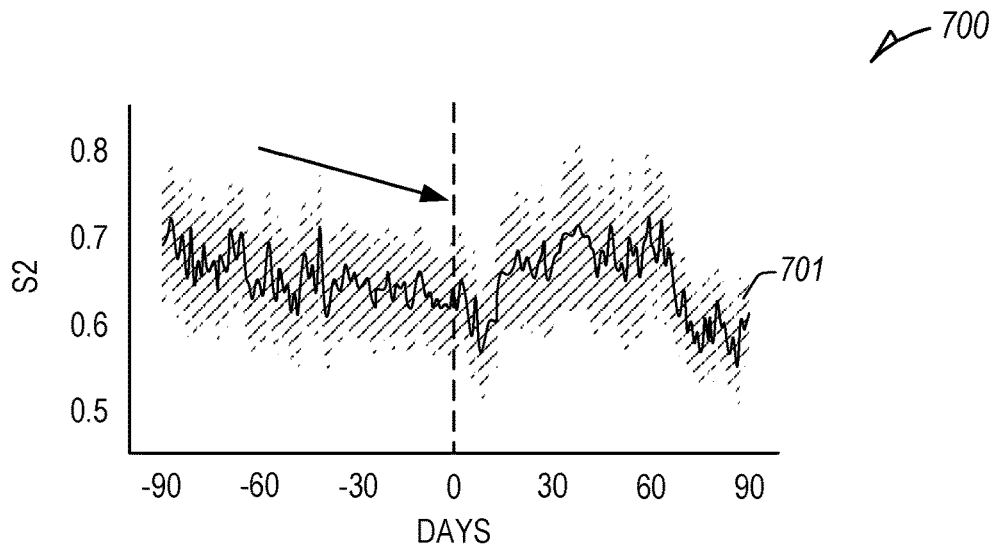

FIG. 7 illustrates an example relationship 700 between the second heart sound (S2) 701, including a trend line and variance, over 180 days centered around a dehydration event (day 0). The arrow in FIG. 7 indicates a gradual downward trend in S2 measurements in the 30 days prior to the dehydration event. In an example, heart sounds, such as S2, can be detected using an implantable accelerometer or microphone, and can be indicative of hemodynamic information, such as indicative of blood pressure, without requiring an implantable blood pressure sensor in the vasculature, an external cuff, etc.

Figure 8:
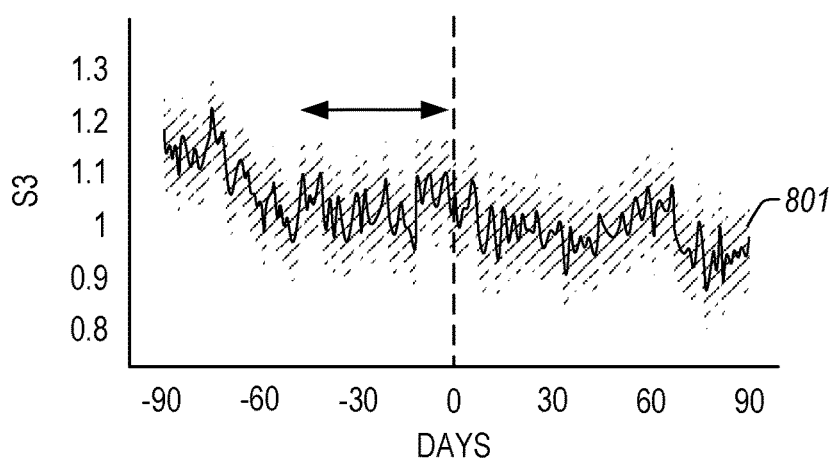

FIG. 8 illustrates an example relationship 800 between the third heart sound (S3) 801, including a trend line and variance, over 180 days centered around a dehydration event (day 0). The arrow in FIG. 8 indicates a general even trend in S3 measurements in the 30 days prior to the dehydration event.

Figure 9:
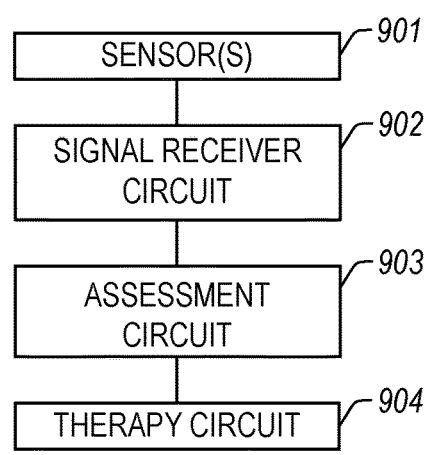
FIG. 9 illustrates an example medical-device system.

FIG. 9 illustrates an example system 900, such as a medical-device system, etc. In an example, one or more aspects of the example system 900 can be a component of, or communicatively coupled to, an ambulatory medical device (AMD). AMDs can be configured to monitor, detect, or treat various physiologic conditions of the body, such as cardiac conditions associated with a reduced ability of a heart to sufficiently deliver blood to a body, including HF, arrhythmias, hypertension, dyssynchrony, etc. AMDs can include a single device or a plurality of medical devices or monitors implanted in a patient's body or otherwise positioned on or about the patient to monitor patient physiologic information of the patient, such as using one or more sensors, the physiologic information including one or more of heart sounds, respiration (e.g., respiration rate, tidal volume (TV), etc.), impedance (e.g., thoracic impedance, cardiac impedance, cutaneous impedance, etc.), pressure (e.g., blood pressure), cardiac activity (e.g., heart rate, cardiac electrical information, etc.), chemical (e.g., electrolyte), physical activity, posture, plethysmography, or one or more other physiologic parameters of a patient, or to provide electrical stimulation or one or more other therapies or treatments to the patient.

The example system 900 can include a signal receiver circuit 902 and an assessment circuit 903. The signal receiver circuit 902 can be configured to receive physiologic information of a patient (or group of patients) from one or more sensors 901. The assessment circuit 903 can be configured to receive information from the signal receiver circuit 902, and to determine one or more parameters (e.g., physiologic parameters, stratifiers, etc.) or patient conditions (e.g., indications of patient dehydration, etc.) using the received physiologic information, such as described herein. The physiologic information can include, among other things, cardiac electrical information, impedance information, respiration information, heart sound information, activity information, posture information, temperature information, chemical information, etc.

In an example, the sensor 901 can include one or more of: a respiration sensor configured to receive respiration information (e.g., a respiration rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a skin temperature sensor; a skin elasticity sensor, or one or more other sensors configured to receive physiologic information of the patient.

The assessment circuit 903 can be configured to provide an output to a user, such as to a display or one or more other user interface, the output including a score, a trend, an alert, or other indication. In other examples, the assessment circuit 903 can be configured to provide an output to another circuit, machine, or process, such as a therapy circuit 904 (e.g., a cardiac resynchronization therapy (CRT) circuit, a chemical therapy circuit, etc.), etc., to control, adjust, or cease a therapy of a medical device, a drug delivery system, etc., or otherwise alter one or more processes or functions of one or more other aspects of a medical-device system, such as one or more CRT parameters, drug delivery, dosage determinations or recommendations, etc. In an example, the therapy circuit 904 can include one or more of a stimulation control circuit, a cardiac stimulation circuit, a dosage determination or control circuit, etc. In other examples, the therapy circuit 904 can be controlled by the assessment circuit 903, or one or more other circuits, etc.

The assessment circuit 903 can be configured to determine a patient condition, including the presence or absence of an arrhythmia event or potential arrhythmia event, an indication of heart failure or worsening heart failure, an indication of patient hydration, dehydration, worsening dehydration status, an indication of patient vomiting, an indication of patient diarrhea, etc., using the received physiologic information.

AMDs can include a range of medical devices, including, for example, traditional cardiac rhythm management (CRM) devices, such as pacemakers, defibrillators, or cardiac resynchronizers, include implantable or subcutaneous devices configured to be implanted in a chest of a patient. The CRM device can include one or more leads to position one or more electrodes or other sensors at various locations in or near the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from the patient, or provide one or more therapies or stimulation to the patient, such as Implantable devices can additionally or separately include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device, however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Each additional sensor within or associated with an AMD or medical device system can increase system cost and complexity, reduce system reliability, or increase the power consumption and reduce the usable life of the AMD. Accordingly, it can be beneficial to use a single sensor to determine multiple types of physiologic information, or a smaller number of sensors to measure a larger number of different types of physiologic information. For example, it can be beneficial to detect atrial cardiac electrical information without a lead or an electrode in, or in contact with, the atria.

Figure 10:
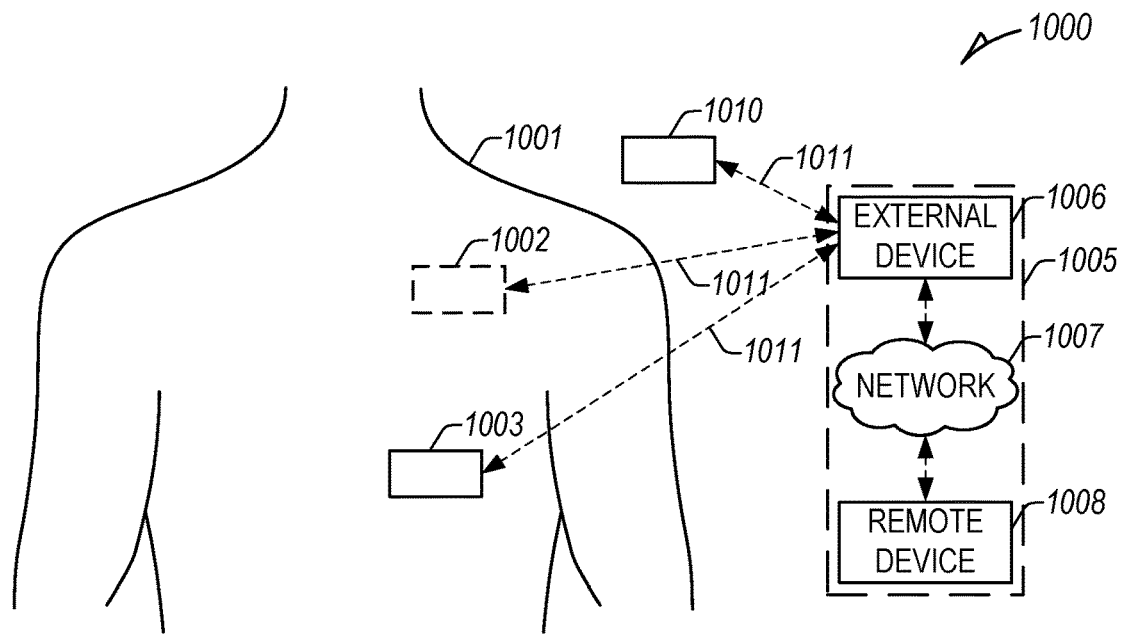
FIG. 10 illustrates an example patient management system and portions of an environment in which the system may operate.

FIG. 10 illustrates an example patient management system 1000 and portions of an environment in which the system 1000 may operate. The patient management system 1000 can perform a range of activities, including remote patient monitoring and diagnosis of a disease condition. Such activities can be performed proximal to a patient 1001, such as in a patient home or office, through a centralized server, such as in a hospital, clinic, or physician office, or through a remote workstation, such as a secure wireless mobile computing device.

The patient management system 1000 can include one or more AMDs, an external system 1005, and a communication link 1011 providing for communication between the one or more AMDs and the external system 1005. The one or more AMDs can include an implantable medical device (IMD) 1002, a wearable medical device 1003, or one or more other implantable, leadless, subcutaneous, external, wearable, or AMDs configured to monitor, sense, or detect information from, determine physiologic information about, or provide one or more therapies to treat various conditions of the patient 1001, such as one or more cardiac or non-cardiac conditions (e.g., dehydration, etc.).

In an example, the IMD 1002 can include one or more traditional cardiac rhythm management (CRM) devices, such as a pacemaker or defibrillator, implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 1001. In another example, the IMD 1002 can include a monitor implanted, for example, subcutaneously in the chest of patient 1001.

The IMD 1002 can include an assessment circuit configured to detect or determine specific physiologic information of the patient 1001, or to determine one or more conditions or provide information or an alert to a user, such as the patient 1001 (e.g., a patient), a clinician, or one or more other caregivers or processes. The IMD 1002 can alternatively or additionally be configured as a therapeutic device configured to treat one or more medical conditions of the patient 1001. The therapy can be delivered to the patient 1001 via the lead system and associated electrodes or using one or more other delivery mechanisms. The therapy can include delivery of one or more drugs to the patient 1001 using the MD 1002 or one or more of the other AMDs. In some examples, therapy can include CRT for rectifying dyssynchrony and improving cardiac function in CHF patients. In other examples, the IMD 1002 can include a drug delivery system, such as a drug infusion pump to deliver drugs to the patient for managing arrhythmias or complications from arrhythmias, hypertension, or one or more other physiologic conditions.

The wearable medical device 1003 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). The wearable medical device 1003 can include an optical sensor configured to detect a PPG signal on a wrist, finger, or other location on the patient 1001. In other examples, the wearable medical device 1003 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 1000 can include, among other things, a respiration sensor configured to receive respiration information (e.g., a respiration rate, a respiration volume (a minute volume (MV), a tidal volume (TV), etc.), etc.), a heart sound sensor configured to receive heart sound information, a thoracic impedance sensor configured to receive impedance information, a cardiac sensor configured to receive cardiac electrical information, an activity sensor configured to receive information about a physical motion (e.g., activity, posture, etc.), a plethysmography sensor, or one or more other sensors configured to receive physiologic information of the patient 1001.

The external system 1005 can include a dedicated hardware/software system, such as a programmer, a remote server-based patient management system, or alternatively a system defined predominantly by software running on a standard personal computer. The external system 1005 can manage the patient 1001 through the MD 1002 or one or more other AMDs connected to the external system 1005 via a communication link 1011. In other examples, the IMD 1002 can be connected to the wearable device 1003, or the wearable device 1003 can be connected to the external system 1005, via the communication link 1011. This can include, for example, programming the IMD 1002 to perform one or more of acquiring physiological data, performing at least one self-diagnostic test (such as for a device operational status), analyzing the physiological data to detect a cardiac arrhythmia, or optionally delivering or adjusting a therapy to the patient 1001. Additionally, the external system 1005 can send information to, or receive information from, the IMD 1002 or the wearable device 1003 via the communication link 1011. Examples of the information can include real-time or stored physiological data from the patient 1001, diagnostic data, such as detection of patient hydration status, hospitalizations, responses to therapies delivered to the patient 1001, or device operational status of the IMD 1002 or the wearable device 1003 (e.g., battery status, lead impedance, etc.). The communication link 1011 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 1005 can include an external device 1006 in proximity of the one or more AMDs, and a remote device 1008 in a location relatively distant from the one or more AMDs, in communication with the external device 1006 via a communication network 1007. Examples of the external device 1006 can include a medical device programmer.

The remote device 1008 can be configured to evaluate collected patient or patient information and provide alert notifications, among other possible functions. In an example, the remote device 1008 can include a centralized server acting as a central hub for collected data storage and analysis. The server can be configured as a uni-, multi-, or distributed computing and processing system. The remote device 1008 can receive data from multiple patients. The data can be collected by the one or more AMDs, among other data acquisition sensors or devices associated with the patient 1001. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more AMDs, such as the IMD. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 1008 may additionally include one or more locally configured clients or remote clients securely connected over the communication network 1007 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 1008, including the server and the interconnected clients, may also execute a follow-up scheme by sending follow-up requests to the one or more AMDs, or by sending a message or other communication to the patient 1001 (e.g., the patient), clinician or authorized third party as a compliance notification.

The communication network 1007 can provide wired or wireless interconnectivity. In an example, the communication network 1007 can be based on the Transmission Control Protocol/Internet Protocol (TCP/IP) network communication specification, although other types or combinations of networking implementations are possible. Similarly, other network topologies and arrangements are possible.

One or more of the external device 1006 or the remote device 1008 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 1006 or the remote device 1008 can include a respective display unit for displaying the physiological or functional signals, or alerts, alarms, emergency calls, or other forms of warnings to signal the detection of arrhythmias. In some examples, the external system 1005 can include an external data processor configured to analyze the physiological or functional signals received by the one or more AMDs, and to confirm or reject the detection of arrhythmias. Computationally intensive algorithms, such as machine-learning algorithms, can be implemented in the external data processor to process the data retrospectively to detect cardia arrhythmias.

Portions of the one or more AMDs or the external system 1005 can be implemented using hardware, software, firmware, or combinations thereof. Portions of the one or more AMDs or the external system 1005 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 1000 can include a therapy device 1010, such as a drug delivery device configured to provide therapy or therapy information (e.g., dosage information, etc.) to the patient 1001, such as using information from one or more of the AMDs. In other examples, one or more of the AMDs can be configured to provide therapy or therapy information to the patient 1001. The therapy device 1010 can be configured to send information to or receive information from one or more of the AMDs or the external system 1005 using the communication link 1011. In an example, the one or more AMDs, the external device 1006, or the remote device 1008 can be configured to control one or more parameters of the therapy device 1010.

The external system 1005 can allow for programming the one or more AMDs and can receives information about one or more signals acquired by the one or more AMDs, such as can be received via a communication link 1011. The external system 1005 can include a local external IMD programmer. The external system 1005 can include a remote patient management system that can monitor patient status or adjust one or more therapies such as from a remote location.

The assessment circuit may be implemented at the external system 1005, which can be configured to perform HF risk stratification such as using data extracted from the one or more AMDs or data stored in a memory within the external system 1005. Portions of patient chronic condition-based HF or other assessment circuit may be distributed between the one or more AMDs and the external system 1005.

Figure 11:
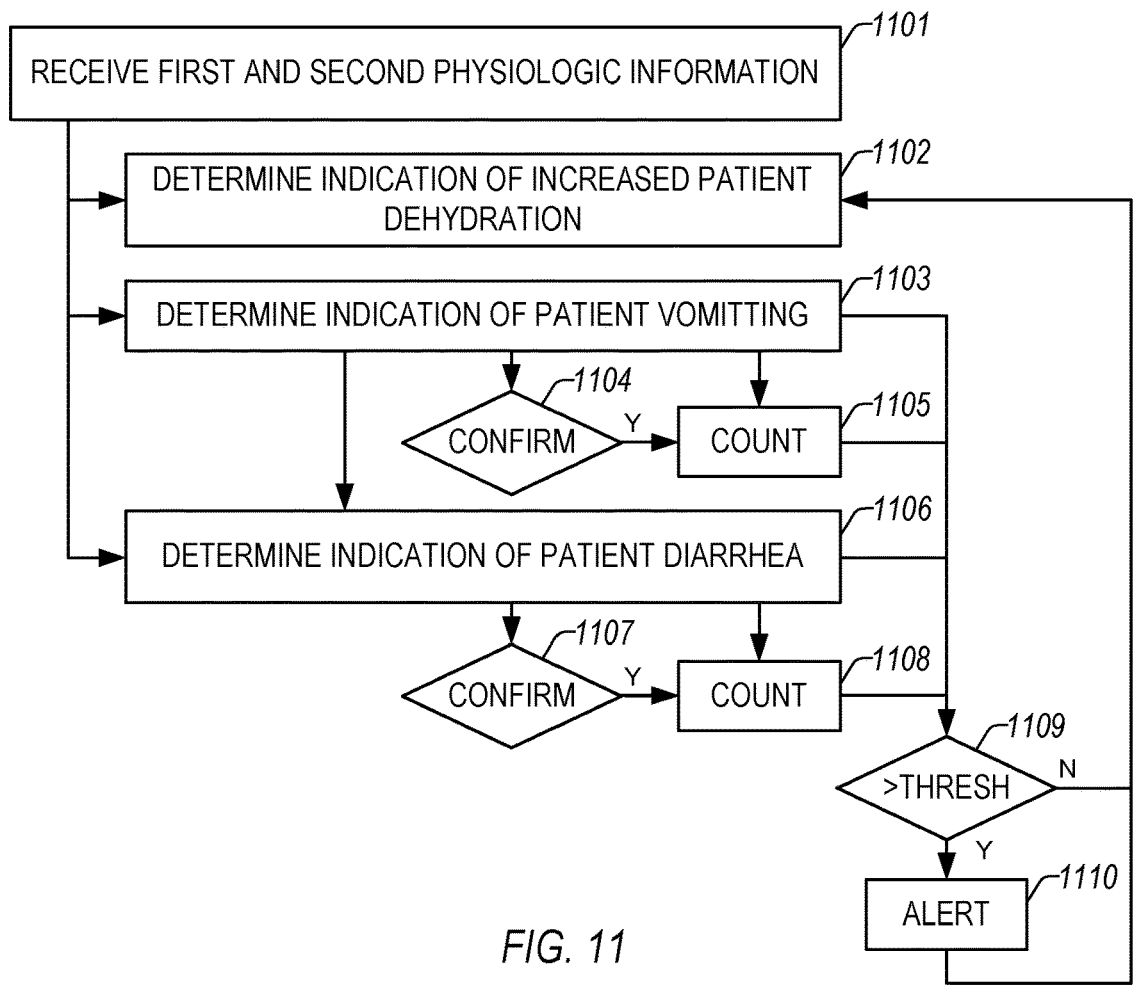
FIG. 11 illustrates a method of determining dehydration, or one or more indications of dehydration, of a patient, such as of a cancer patient undergoing chemotherapy treatment.

FIG. 11 illustrates a method 1100 of determining dehydration, or one or more indications of increased dehydration, of a patient, such as of a cancer patient undergoing chemotherapy treatment. In an example, the method can be performed by a system, such as a medical device system (e.g., the patient management system 1000 illustrated in FIG. 10, etc.) including one or more AMDs (e.g., implantable, subcutaneous, wearable, external, etc.), an external system, one or more therapy devices, etc., such as described herein.

At 1101, physiologic information can be received from the patient, such as at a signal receiver circuit of a system, from one or more implantable, wearable, or external sensors. In an example, the one or more sensors can be components of the medical device system. In other examples, the one or more sensors can be separate from the medical device system comprising the signal receiver circuit.

In an example, the physiologic information can include separate first and second physiologic information, or additional physiologic information, from the patient. For example, the first physiologic information can include heart sound information of the patient. In an example, the heart sound information can be sensed using an accelerometer, and information about one or more major sounds (e.g., a time, an amplitude, an energy, etc.) can be detected, such as using a heart sound detector circuit (e.g., the assessment circuit, etc.). In other examples, the first physiologic information can include other information, such as that illustrated in Table 2 or otherwise described herein, detected using one or more sensors and/or detector circuits (e.g., the assessment circuit, etc.). The second physiologic information can include information separate from the first physiologic information (e.g., the first physiologic information can include HS information and the second physiologic information can include impedance information, respiration information, etc.). In other examples, the physiologic information can include additional information separate from the first and second physiologic information, such as posture information, activity information, HR information, or one or more other types of physiologic information described herein.

At 1102, an indication of hydration is determined, such as an indication of increased patient dehydration using the received first and second physiologic information. The indication can be determined using an assessment circuit, such as according to one or more of the relationships disclosed herein (e.g., Table 2, FIGS. 2-8, etc.). In an example, the first physiologic information can be used to qualify the second physiologic information, or vice versa. In other examples, the first and second physiologic information can be unqualified. The indication of hydration can be patient-specific, indicating an increase in dehydration of the patient with respect to a previous hydration level. Comparisons of the first or second physiologic information (or other physiologic information) to one or more thresholds can include comparisons to one or more levels, rates of change, etc., such illustrated in FIGS. 2-8, as otherwise described herein, etc.

In an example, the indication of increased patient hydration can be determined using the first physiologic information in response to the second physiologic information meeting a predetermined criterion (e.g., qualified physiologic information). For example, the first physiologic information can include third heart sound (S3) information of the patient, the second physiologic information can include impedance information of the patient, and the predetermined criterion can include when a change in the S3 information is below a threshold, such as within a percentage (e.g., 25%, etc.) of a baseline (e.g., a long-term or short-term average, etc.). The indication of increased patient hydration can be determined using a change in the impedance information (e.g., a decrease in transthoracic impedance, etc., above a threshold) when the change in S3 information is below the threshold (e.g., remains unchanged).

In other examples, the first physiologic information can include second heart sound (S2) information of the patient, the second physiologic information can include at least one of posture information or activity information of the patient, and the predetermined criterion can include when the posture information indicates a change in patient posture or when the activity information indicates that the patient activity is below a threshold. The indication of increased patient hydration can be determined using a change in the S2 information of the patient (e.g., a decrease in S2 trend, a decrease in S2 value, such as a daily or short-term S2 value, below a long-term S2 value, etc.) when the posture information indicates a change in patient posture (e.g., from standing to sitting, sitting to lying down, standing to lying down, or vice-versa, etc.) or when the activity information indicates that patient activity is below a threshold (e.g., when the patient is inactive, etc.).

At 1103, an indication of patient vomiting can be determined, such as using one or more of the first or second physiologic information, or other physiologic information (e.g., a combination of two or more of heart sound information, respiration information, impedance information, etc.). For example, the indication of patient vomiting can be determined using an acute increase in S2 value in combination with an acute decrease in S1 value. In certain examples, the determination can be supplemented with corresponding changes in posture (e.g., leaning forward during dry heaving and emission), increases in HR and respiration rate after or in a time period around (e.g., 30 seconds, etc.) detected heart sound changes. The indication can be determined using the assessment circuit.

At 1104, the determined indication can be confirmed, such as by the patient, a clinician, or other caregiver using a remote device, an input to an AMD, etc. In an example, determination of an indication of patient vomiting can trigger requested confirmation, such as from the patient, a clinician, or one or more other caregivers or users associated with the patient. At 1105, a count of determined vomiting events can be aggregated and stored, such as using the assessment circuit. The count can include events confirmed at 1104, determined at 1103, etc. In certain examples, multiple counts can be stored, such as determined events, confirmed events, etc. Such information can be provided to a clinician, or used by the assessment circuit to adjust or improve candidate event determination, such as by increasing detection sensitivity, specificity, adjusting one or more thresholds, etc. In an example, a number of events, confirmed events, or not-confirmed events can be used to provide an alert, such as to a user, clinician, caregiver, or one or more other system components or processes.

At 1106, an indication of patient diarrhea (e.g., a stool event) can be determined, such as using one or more of the first or second physiologic information, or other physiologic information (e.g., BP, S2 amplitude, or HR that coincides with a respiratory pause, etc.). The indication can be determined using the assessment circuit. At 1107, the determined indication can be confirmed, such as by the patient, a clinician, or other caregiver using a remote device, an input to an AMD, etc. In an example, determination of an indication of patient diarrhea can trigger requested confirmation, such as from the patient, a clinician, or one or more other caregivers or users associated with the patient. At 1108, a count of determined diarrhea events can be aggregated and stored, such as using the assessment circuit. The count of determined diarrhea events can be aggregated, such as per day. A severity grade can be determined using the count. The count can include events confirmed at 1107, determined at 1106, etc. In certain examples, multiple counts can be stored, such as determined events, confirmed events, etc. Such information can be provided to a clinician or used by the assessment circuit to adjust or improve candidate event determination, such as by increasing detection sensitivity, specificity, adjusting one or more thresholds, etc., in certain examples, commensurate with the determined severity grade.

In certain examples, one or more of the determined indication of patient vomiting at 1103, the confirmed indication at 1104, one or more counts at 1105, the determined indication of patient diarrhea at 1106, the confirmed indication at 1107, or one or more counts at 1108 can be used to determine, supplement, or adjust the indication of increased patient dehydration at 1102. At 1109, one or more of the determined indication of patient vomiting at 1103, the confirmed indication at 1104, one or more counts at 1105, the determined indication of patient diarrhea at 1106, the confirmed indication at 1107, or one or more counts at 1108 can be compared to one or more thresholds (e.g., a vomiting threshold, such as a daily or other time period vomiting threshold, confirmed or unconfirmed, etc.; a diarrhea threshold, such as a daily or other time period diarrhea threshold, confirmed or unconfirmed, etc.; etc.). If the threshold is met or exceeded at 1109, an alert can be provided at 1110, such as by the assessment circuit or one or more other circuits to a user, clinician, caregiver, or one or more other system components or processes.

Figure 12:
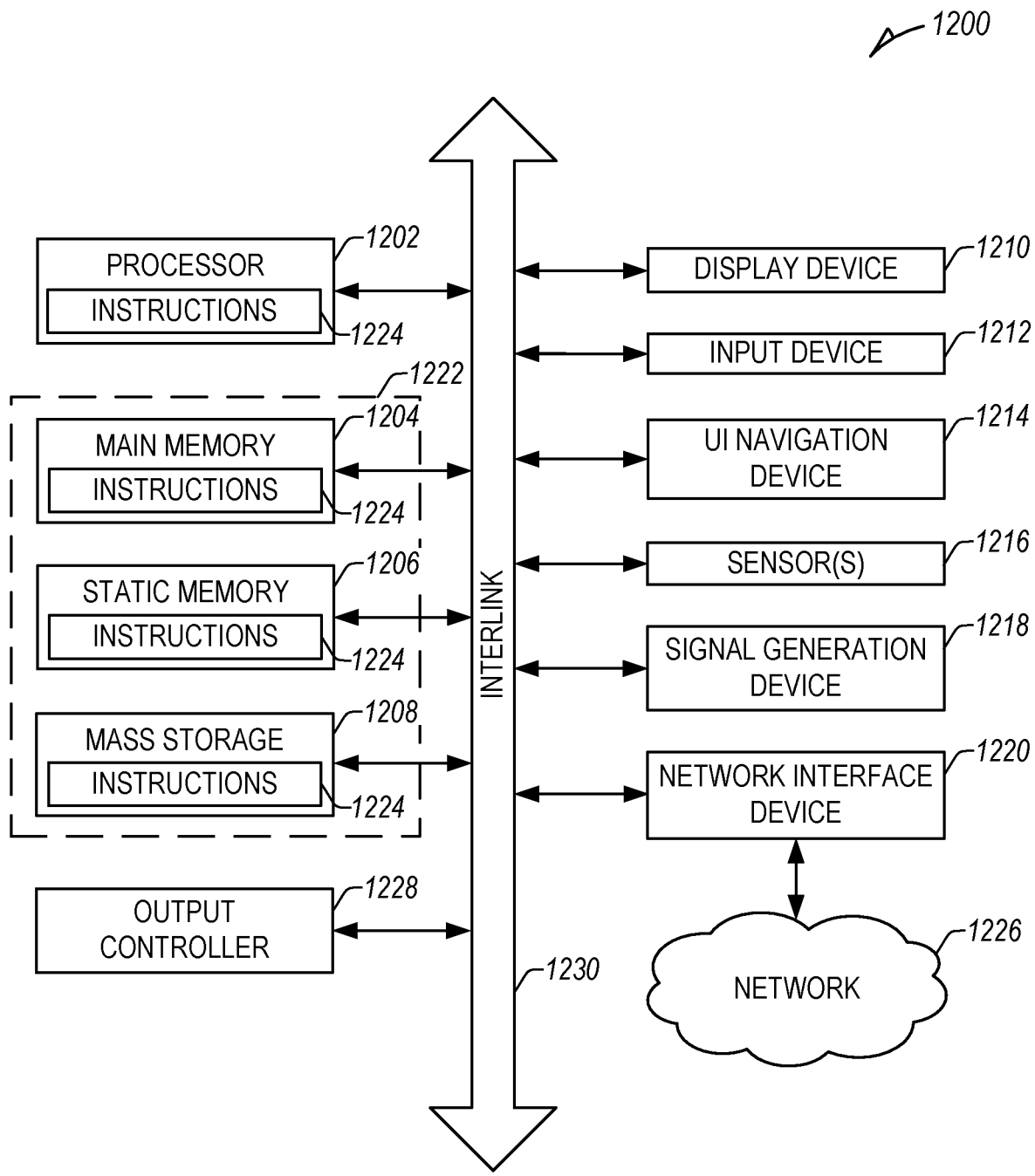
FIG. 12 illustrates a block diagram of an example machine upon which any one or more of the techniques (e.g., methodologies) discussed herein may perform.

FIG. 12 illustrates a block diagram of an example machine 1200 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 1200. Circuitry (e.g., processing circuitry, an assessment circuit, etc.) is a collection of circuits implemented in tangible entities of the machine 1200 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 1200 follow.

In alternative embodiments, the machine 1200 may operate as a standalone device or may be connected (e.g., networked) to other machines. In a networked deployment, the machine 1200 may operate in the capacity of a server machine, a client machine, or both in server-client network environments. In an example, the machine 1200 may act as a peer machine in peer-to-peer (P2P) (or other distributed) network environment. The machine 1200 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 1200 may include a hardware processor 1202 (e.g., a central processing unit (CPU), a graphics processing unit (GPU), a hardware processor core, or any combination thereof), a main memory 1204, a static memory (e.g., memory or storage for firmware, microcode, a basic-input-output (BIOS), unified extensible firmware interface (UEFI), etc.) 1206, and mass storage 1208 (e.g., hard drive, tape drive, flash storage, or other block devices) some or all of which may communicate with each other via an interlink (e.g., bus) 1230. The machine 1200 may further include a display unit 1210, an alphanumeric input device 1212 (e.g., a keyboard), and a user interface (UI) navigation device 1214 (e.g., a mouse). In an example, the display unit 1210, input device 1212, and UI navigation device 1214 may be a touch screen display. The machine 1200 may additionally include a signal generation device 1218 (e.g., a speaker), a network interface device 1220, and one or more sensors 1216, such as a global positioning system (GPS) sensor, compass, accelerometer, or one or more other sensors. The machine 1200 may include an output controller 1228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 1202, the main memory 1204, the static memory 1206, or the mass storage 1208 may be, or include, a machine-readable medium 1222 on which is stored one or more sets of data structures or instructions 1224 (e.g., software) embodying or utilized by any one or more of the techniques or functions described herein. The instructions 1224 may also reside, completely or at least partially, within any of registers of the processor 1202, the main memory 1204, the static memory 1206, or the mass storage 1208 during execution thereof by the machine 1200. In an example, one or any combination of the hardware processor 1202, the main memory 1204, the static memory 1206, or the mass storage 1208 may constitute the machine-readable medium 1222. While the machine-readable medium 1222 is illustrated as a single medium, the term "machine-readable medium" may include a single medium or multiple media (e.g., a centralized or distributed database, and/or associated caches and servers) configured to store the one or more instructions 1224.

The term "machine-readable medium" may include any medium that is capable of storing, encoding, or carrying instructions for execution by the machine 1200 and that cause the machine 1200 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1224 may be further transmitted or received over a communications network 1226 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1220 may include one or more physical jacks (e.g., Ethernet, coaxial, or phone jacks) or one or more antennas to connect to the communications network 1226. In an example, the network interface device 1220 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 1200, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for determining patient dehydration during cancer therapy, comprising:
   a signal receiver circuit configured to receive first and second physiologic information of a patient, the first physiologic information comprising heart sound information of the patient, and the second physiologic information comprising information different than the first physiologic information; and
   an assessment circuit, coupled to a therapy circuit, the assessment circuit configured to:
      determine an indication of patient dehydration associated with cancer therapy using the received first and second physiologic information; and
      provide cancer therapy adjustment information at an output based on the determined indication of patient dehydration.

2. The system of claim 1, wherein the assessment circuit is configured to determine the indication of patient dehydration using the second physiologic information in response to the first physiologic information meeting a predetermined criterion.

3. The system of claim 2, wherein the heart sound information of the patient comprises third heart sound (S3)

information of the patient, and wherein the predetermined criterion includes a maintained S3 of the patient over a number of previous days,
> wherein the second physiologic information comprises impedance information of the patient, and
> wherein to determine the indication of patient dehydration, the assessment circuit is configured to:
> > determine a change in S3 information of the patient over a number of days; and
> > determine the indication of patient dehydration using the impedance information in response to the determined change in S3 information not exceeding a baseline S3 value by more than a threshold.

4. The system of claim 2, wherein the heart sound information of the patient comprises second heart sound (S2) information of the patient,
> wherein the second physiologic information comprises at least one of posture or activity information of the patient, and
> wherein the assessment circuit is configured to determine the indication of patient dehydration using the S2 information of the patient when the posture information indicates a change in patient posture or when the activity information indicates that patient activity is below a threshold.

5. The system of claim 1, wherein the heart sound information comprises second heart sound (S2) information of the patient, and
> wherein the second physiologic information comprises at least one of heart rate information of the patient, respiration information of the patient, impedance information of the patient, or chemical information of the patient.

6. The system of claim 1, wherein the signal receiver circuit is configured to receive at least one of respiration information of the patient or impedance information of the patient, and
> wherein, to determine the patient dehydration, the assessment circuit is configured to determine an indication of patient vomiting using the first physiologic information and the respiration information of the patient or the impedance information of the patient.

7. The system of claim 6, wherein the assessment circuit is configured to trigger patient confirmation of a candidate patient vomiting event using the determined indication of patient vomiting.

8. The system of claim 6, wherein the assessment circuit is configured to count candidate patient vomiting events using determined indications of patient vomiting, and to adjust the determined indication of patient dehydration using the count of candidate patient vomiting events.

9. The system of claim 1, wherein the signal receiver circuit is configured to receive heart rate (HR) information of the patient, and
> wherein, to determine the patient dehydration, the assessment circuit is configured to determine an indication of patient diarrhea using the first physiologic information and the heart rate (HR) information of the patient.

10. The system of claim 9, wherein the assessment circuit is configured to trigger patient confirmation of a candidate diarrhea events using the determined indication of patient diarrhea.

11. The system of claim 9, wherein the assessment circuit is configured to count candidate patient diarrhea events using determined indications of patient diarrhea, and to adjust the determined indication of patient dehydration using the count of candidate patient diarrhea events.

12. The system of claim 1, comprising an implantable medical device comprising a heart sound sensor,
> wherein, to determine the patient dehydration, the assessment circuit is configured to determine an indication of patient vomiting and an indication of patient diarrhea using the first physiologic information.

13. A system, comprising:
> a signal receiver circuit configured to receive first and second physiologic information of a patient, the first physiologic information comprising heart sound information of the patient, and the second physiologic information comprising at least one of respiration information of the patient or impedance information of the patient; and
> an assessment circuit configured to determine an indication of patient vomiting using the received first and second physiologic information, including the heart sound information of the patient and at least one of respiration information of the patient or the impedance information of the patient.

14. The system of claim 13, wherein the assessment circuit is configured to trigger patient confirmation of a candidate patient vomiting event using the determined indication of patient vomiting.

15. The system of claim 13, wherein the assessment circuit is configured to count candidate patient vomiting events using determined indications of patient vomiting, and to determine an indication of patient dehydration using the count of candidate patient vomiting events.

16. The system of claim 13, wherein the first physiologic information comprises third heart sound (S3) information of the patient, and
> wherein the second physiologic information comprises impedance information of the patient.

17. The system of claim 13, wherein the second physiologic information comprises respiration information of the patient.

18. A system, comprising:
> a signal receiver circuit configured to receive first and second physiologic information of a patient, the first physiologic information comprising heart sound information of the patient, and the second physiologic information comprising heart rate (HR) information of the patient; and
> an assessment circuit configured to determine an indication of patient diarrhea using the received first and second physiologic information, including the heart sound information of the patient and the HR information of the patient.

19. The system of claim 18, wherein the assessment circuit is configured to trigger patient confirmation of a candidate diarrhea events using the determined indication of patient diarrhea.

20. The system of claim 18, wherein the assessment circuit is configured to count candidate patient diarrhea events using determined indications of patient diarrhea, and to determine an indication of patient dehydration using the count of candidate patient diarrhea events.

\* \* \* \* \*